(12) United States Patent
O'Neill et al.

(10) Patent No.: US 6,362,327 B1
(45) Date of Patent: Mar. 26, 2002

(54) HIGH LEVEL EXPRESSION OF HUMAN CYCLOOXYGENASE-2

(75) Inventors: Gary P. O'Neill, Dollard des Ormeaux; Joseph A. Mancini, St. Leonard, both of (CA)

(73) Assignee: Merck Frosst Canada & Co., Province of Nova Scotia (CA)

( * ) Notice: Subject to any disclaimer, the term of this patent is extended or adjusted under 35 U.S.C. 154(b) by 0 days.

(21) Appl. No.: 09/599,781

(22) Filed: Jun. 21, 2000

Related U.S. Application Data

(63) Continuation of application No. 08/930,589, filed as application No. PCT/CA94/00501 on Sep. 13, 1994, now Pat. No. 6,107,087, which is a continuation of application No. 08/084,033, filed on Sep. 27, 1993, now abandoned, and a continuation-in-part of application No. 08/064,271, filed on May 6, 1993, now Pat. No. 5,543,297, which is a continuation-in-part of application No. 07/994,760, filed on Dec. 22, 1992, now abandoned.

(51) Int. Cl.[7] ............................................. C07H 21/04
(52) U.S. Cl. .................................... 536/23.5; 536/23.1
(58) Field of Search .............................. 536/23.1, 23.2, 536/23.5; 435/325, 252.33, 189, 300.1

(56) References Cited

PUBLICATIONS

Funk et al. "Human platelet/erythroleukemia cell prostaglandin G/H synthase:cDNA cloning . . . " FASEB Journal 5, 2304–2312, Jun. 1991.*

\* cited by examiner

*Primary Examiner*—Nashaat T. Nashed
(74) *Attorney, Agent, or Firm*—Joseph A. Coppola; Jack L. Tribble

(57) ABSTRACT

The invention discloses a cDNA consisting of human cyclooxygenase-2 cDNA attached to 3' flanking sequence of human cyclooxygenase-1 methods for increasing the expression of human cyclooxygenase-2 in transformed cells and assays for preferentially and independently measuring cyclogenase-2 in samples.

1 Claim, 7 Drawing Sheets

Met Leu Ala Arg Ala Leu Leu Leu Cys Ala Val Leu Ala Leu Ser His
1          5                    10                  15

Thr Ala Asn Pro Cys Cys Ser His Pro Cys Gln Asn Arg Gly Val Cys
             20              25              30

Met Ser Val Gly Phe Asp Gln Tyr Lys Cys Asp Cys Thr Arg Thr Gly
         35              40              45

Phe Tyr Gly Glu Asn Cys Ser Thr Pro Glu Phe Leu Thr Arg Ile Lys
     50              55              60

Leu Phe Leu Lys Pro Thr Pro Asn Thr Val His Tyr Ile Leu Thr His
65              70              75                  80

Phe Lys Gly Phe Trp Asn Val Val Asn Asn Ile Pro Phe Leu Arg Asn
             85              90              95

Ala Ile Met Ser Tyr Val Leu Thr Ser Arg Ser His Leu Ile Asp Ser
             100             105             110

Pro Pro Thr Tyr Asn Ala Asp Tyr Gly Tyr Lys Ser Trp Glu Ala Phe
         115             120             125

Ser Asn Leu Ser Tyr Tyr Thr Arg Ala Leu Pro Pro Val Pro Asp Asp
         130             135             140

Cys Pro Thr Pro Leu Gly Val Lys Gly Lys Lys Gln Leu Pro Asp Ser
145             150             155             160

Asn Glu Ile Val Glu Lys Leu Leu Leu Arg Arg Lys Phe Ile Pro Asp
             165             170             175

Pro Gln Gly Ser Asn Met Met Phe Ala Phe Ala Gln His Phe Thr
         180             185             190

His Gln Phe Phe Lys Thr Asp His Lys Arg Gly Pro Ala Phe Thr Asn
         195             200             205

Gly Leu Gly His Gly Val Asp Leu Asn His Ile Tyr Gly Glu Thr Leu
         210             215             220

FIG.1A

```
Ala Arg Gln Arg Lys Leu Arg Leu Phe Lys Asp Gly Lys Met Lys Tyr
225               230               235               240

Gln Ile Ile Asp Gly Glu Met Tyr Pro Pro Thr Val Lys Asp Thr Gln
            245               250               255

Ala Glu Met Ile Tyr Pro Pro Gln Val Pro Glu His Leu Arg Phe Ala
            260               265               270

Val Gly Gln Glu Val Phe Gly Leu Val Pro Gly Leu Met Met Tyr Ala
            275               280               285

Thr Ile Trp Leu Arg Glu His Asn Arg Val Cys Asp Val Leu Lys Gln
            290               295               300

Glu His Pro Glu Trp Gly Asp Glu Gln Leu Phe Gln Thr Ser Arg Leu
305               310               315               320

Ile Leu Ile Gly Glu Thr Ile Lys Ile Val Ile Glu Asp Tyr Val Gln
            325               330               335

His Leu Ser Gly Tyr His Phe Lys Leu Lys Phe Asp Pro Glu Leu Leu
            340               345               350

Phe Asn Lys Gln Phe Gln Tyr Gln Asn Arg Ile Ala Ala Glu Phe Asn
            355               360               365

Thr Leu Tyr His Trp His Pro Leu Leu Pro Asp Thr Phe Gln Ile His
            370               375               380

Asp Gln Lys Tyr Asn Tyr Gln Gln Phe Ile Tyr Asn Asn Ser Ile Leu
385               390               395               400

Leu Glu His Gly Ile Thr Gln Phe Val Glu Ser Phe Thr Arg Gln Ile
            405               410               415

Ala Gly Arg Val Ala Gly Gly Arg Asn Val Pro Pro Ala Val Gln Lys
            420               425               430
```

FIG.1B

Val Ser Gln Ala Ser Ile Asp Gln Ser Arg Gln Met Lys Tyr Gln Ser
          435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
              485                 490                 495

Lys Pro Arg Pro Asp Ala Ile Phe Gly Glu Thr Met Val Glu Val Gly
              500                 505                 510

Ala Pro Phe Ser Leu Lys Gly Leu Met Gly Asn Val Ile Cys Ser Pro
          515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
              565                 570                 575

Val Thr Ile Asn Ala Ser Ser Ser Arg Ser Gly Leu Asp Ile Asn
              580                 585                 590

Pro Thr Val Leu Leu Lys Glu Arg Ser Thr Glu Leu
          595                 600

FIG.1C

```
GTCCAGGAAC TCCTCAGCAG CGCCTCCTTC AGCTCCACAG CCAGACGCCC TCAGACAGCA    60

AAGCCTACCC CCGCGCCGCG CCCTGCCCGC CGCTGCGATG CTCGCCCGCG CCCTGCTGCT   120

GTGCGCGGTC CTGGCGCTCA GCCATACAGC AAATCCTTGC TGTTCCCACC CATGTCAAAA   180

CCGAGGTGTA TGTATGACTG TGGGATTTGA CCAGTATAAG TGCGATTGTA CCCGGACAGG   240

ATTCTATGGA GAAAACTGCT CAACACCGGA ATTTTGACA AGAATAAAAT TATTTCTGAA    300

ACCCACTCCA AACACAGTGC ACTACATACT TACCCACTTC AAGGGATTTT GGAACGTTGT   360

GAATAACATT CCCTTCCTTC GAAATGCAAT TATGAGTTAT GTGTTGACAT CCAGATCACA   420

TTTGATTGAC AGTCCACCAA CTTACAATGC TGACTATGGC TACAAAAGCT GGGAAGCCTT   480

CTCTAACCTC TCCTATTATA CTAGAGCCCT TCCTCCTGTG CCTGATGATT GCCCGACTCC   540

CTTGGGTGTC AAAGGTAAAA AGCAGCTTCC TGATTCAAAT GAGATTGTGG AAAAAATTGCT  600

TCTAAGAAGA AAGTTCATCC CTGATCCCCA GGGCTCAAAC ATGATGTTTG CATTCTTTGC   660

CCAGCACTTC ACGCACCAGT TTTTCAAGAC AGATCATAAG CGAGGGCCAG CTTTCACCAA   720

CGGGCTGGGC CATGGGGTGG ACTTAAATCA TATTTACGGT GAAACTCTGG CTAGACAGCG   780

TAAACTGCGC CTTTTCAAGG ATGGAAAAAT GAAATATCAG ATAATTGATG GAGAGATGTA   840

TCCTCCCACA GTCAAAGATA CTCAGGCAGA GATGATCTAC CCTCCTCAAG TCCCTGAGCA   900

TCTACGGTTT GCTGTGGGGC AGGAGGTCTT TGGTCTGGTG CCTGGTCTGA TGATGTATGC   960

CACAATCTGG CTGCGGGAAC ACAACAGAGT ATGTGATGTG CTTAAACAGG AGCATCCTGA  1020

ATGGGGTGAT GAGCAGTTGT TCCAGACAAG CAGGCTAATA CTGATAGGAG AGACTATTAA  1080

GATTGTGATT GAAGATTATG TGCAACACTT GAGTGGCTAT CACTTCAAAC TGAAATTTGA  1140

CCCAGAACTA CTTTTCAACA AACAATTCCA GTACCAAAAT CGTATTGCTG CTGAATTTAA  1200
```

FIG.2A

```
CACCCTCTAT CACTGGCATC CCCTTCTGCC TGACACCTTT CAAATTCATG ACCAGAAATA 1260

CAACTATCAA CAGTTTATCT ACAACAACTC TATATTGCTG AACATGGAA TTACCCAGTT 1320

TGTTGAATCA TTCACCAGGC AAATTGCTGG CAGGGTTGCT GGTGGTAGGA ATGTTCCACC 1380

CGCAGTACAG AAAGTATCAC AGGCTTCCAT TGACCAGAGC AGGCAGATGA ATACCAGTC 1440

TTTTAATGAG TACCGCAAAC GCTTTATGCT GAAGCCCTAT GAATCATTTG AAGAACTTAC 1500

AGGAGAAAAG GAAATGTCTG CAGAGTTGGA AGCACTCTAT GGTGACATCG ATGCTGTGGA 1560

GCTGTATCCT GCCCTTCTGG TAGAAAAGCC TCGGCCAGAT GCCATCTTTG GTGAAACCAT 1620

GGTAGAAGTT GGAGCACCAT TCTCCTTGAA AGGACTTATG GGTAATGTTA TATGTTCTCC 1680

TGCCTACTGG AAGCCAAGCA CTTTTGGTGG AGAAGTGGGT TTTCAAATCA TCAACACTGC 1740

CTCAATTCAG TCTCTCATCT GCAATAACGT GAAGGGCTGT CCCTTTACTT CATTCAGTGT 1800

TCCAGATCCA GAGCTCATTA AAACAGTCAC CATCAATGCA AGTTCTTCCC GCTCCGGACT 1860

AGATGATATC AATCCCACAG TACTACTAAA AGAACGGTCG ACTGAACTGT AGAAGTCTAA 1920

TGATCATATT TATTTATTTA TATGAACCAT GTCTATTAAT TTAATTATTT AATAATATTT 1980

ATATTAAACT CCTTATGTTA CTTAACATCT TCTGTAACAG AAGTCAGTAC TCCTGTTGCG 2040

GAGAAAGGAG TCATACTTGT GAAGACTTTT ATGTCACTAC TCTAAAGATT TTGCTGTTGC 2100

TGTTAAGTTT GGAAAACAGT TTTTATTCTG TTTTATAAAC CAGAGAGAAA TGAGTTTTGA 2160

CGTCTTTTTA CTTGAATTTC AACTTATATT ATAAGGACGA AAGTAAAGAT GTTTGAATAC 2220

TTAAACACTA TCACAAGATG CCAAAATGCT GAAAGTTTTT ACACTGTCGA TGTTTCCAAT 2280

GCATCTTCCA TGATGCATTA GAAGTAACTA ATGTTTGAAA TTTTAAAGTA CTTTTGGGTA 2340

TTTTTCTGTC ATCAAACAAA ACAGGTATCA GTGCATTATT AAATGAATAT TTAAATTAGA 2400
```

FIG.2B

```
CATTACCAGT AATTTCATGT CTACTTTTTA AAATCAGCAA TGAAACAATA ATTTGAAATT  2460

TCTAAATTCA TAGGGTAGAA TCACCTGTAA AAGCTTGTTT GATTTCTTAA AGTTATTAAA  2520

CTTGTACATA TACCAAAAAG AAGCTGTCTT GGATTTAAAT CTGTAAAATC AGATGAAATT  2580

TTACTACAAT TGCTTGTTAA AATATTTTAT AAGTGATGTT CCTTTTTCAC CAAGAGTATA  2640

AACCTTTTTA GTGTGACTGT TAAAACTTCC TTTTAAATCA AAATGCCAAA TTTATTAAGG  2700

TGGTGGAGCC ACTGCAGTGT TATCTCAAAA TAAGAATATC CTGTTGAGAT ATTCCAGAAT  2760

CTGTTTATAT GGCTGGTAAC ATGTAAAAAC CCCATAACCC CGCCAAAAGG GGTCCTACCC  2820

TTGAACATAA AGCAATAACC AAAGGAGAAA AGCCCAAATT ATTGGTTCCA AATTTAGGGT  2880

TTAAACTTTT TGAAGCAAAC TTTTTTTTAG CCTTGTGCAC TGCAGACCTG GTACTCAGAT  2940

TTTGCTATGA GGTTAATGAA GTACCAAGCT GTGCTTGAAT AACGATATGT TTTCTCAGAT  3000

TTTCTGTTGT ACAGTTTAAT TTAGCAGTCC ATATCACATT GCAAAAGTAG CAATGACCTC  3060

ATAAAATACC TCTTCAAAAT GCTTAAATTC ATTTCACACA TTAATTTTAT CTCAGTCTTG  3120

AAGCCAATTC AGTAGGTGCA TTGGAATCAA GCCTGGCTAC CTGCATGCTG TTCCTTTTCT  3180

TTTCTTCTTT TAGCCATTTT GCTAAGAGAC ACAGTCTTCT CAAACACTTC GTTCTCCTA  3240

TTTTGTTTTA CTAGTTTTAA GATCAGAGTT CACTTTCTTT GGACTCTGCC TATATTTTCT  3300

TACCTGAACT TTTGCAAGTT TTCAGGTAAA CCTCAGCTCA GGaCTGCTAT TTAGCTCCTC  3360

TTAAGAAGAT TAAAAAAAAA AAAAAAG                                      3387
```

FIG.2C

```
1     GGGGC AGGAAAGCAG CATTCTGGAG GGGAGAGCTT TGTGCTTGTC
46    ATTCCAGAGT GCTGAGGCCA GGGCTGATGG TCTTAAATGC TCATTTTCTG
96    GTTTGGCATG GTGAGTGTTG GGGTTGACAT TTAGAACTTT AAGTCTCACC
146   CATTATCTGG AATATTGTGA TTCTGTTTAT CTTCCAGAA TGCTGAACTC
196   CTTGTTAGCC CTTCAGATTG TTAGGAGTGG TTCTCATTTG GTCTGCCAGA
246   ATACTGGGTT CTTAGTTGAC AACCTAGAAT GTCAGATTTC TGGTTGATTT
296   GTAACACAGT CATTCTAGGA TGTGGAGCTA CTGATGAAAT CTGCTAGAAA
346   GTTAGGGGGT TCTTATTTTG CATTCCAGAA TCTTGACTTT CTGATTGGTG
396   ATTCAAAGTG TTGTGTTCCC TGGCTGATGA TCCAGAACAG TGGCTCGTAT
446   CCCAAATCTG TCAGCATCTG GCTGTCTAGA ATGTGGATTT GATTCATTTT
496   CCTGTTCAGT GAGATATCAT AGAGACGGAG ATCCTAAGGT CCAACAAGAA
546   TGCATTCCCT GAATCTGTGC CTGCACTGAG AGGGCAAGGA AGTGGGCTGT
596   TCTTCTTGGG ACCCCCACTA AGACCCTGGT CTGAGGATGT AGAGAGAACA
646   GGTGGGCTGT ATTCACGCCA TTGGTTGGAA GCTACCAGAG CTCTATCCCC
696   ATCCAGGTCT TGACTCATGG CAGCTGTTTC TCATGAAGCT AATAAAATTC
746   GCCC
```

FIG.3

HIGH LEVEL EXPRESSION OF HUMAN CYCLOOXYGENASE-2

This application is a continuation of U.S. patent application Ser. No. 08/930,589, filed Feb. 22, 1996, now U.S. Pat. No. 6,107,087, which is the U.S. national phase of International Patent Application PCT/CA94/00501, filed Sep. 13, 1994, which is a continuation of U.S. patent application Ser. No. 08/084,033, filed Sep. 27, 1993, now abandoned, and is a continuation-in-part of U.S. patent application Ser. No. 08/064,271, filed May 6, 1993, now U.S. Pat. No. 5,543,297, which is a continuation-in-part of U.S. patent application Ser. No. 07/994,760, filed Dec. 22, 1992, now abandoned, the disclosures of which are incorporated herein by reference, in their entirety.

BACKGROUND OF THE INVENTION

The invention encompasses a system for high level expression of human cyclooxygenase-2 protein including a high expression human cyclooxygenase-2 (COX-2) cDNA and mammalian expression vectors.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Until recently, only one form of cyclooxygenase had been characterized, this corresponding to cyclooxygenase-1 (COX-1), a constitutive enzyme originally identified in bovine seminal vesicles. More recently the gene for an inducible form of cyclooxygenase (cyclooxygenase-2; COX-2)) has been cloned, sequenced and characterized from chicken, murine and human sources. Cyclooxygenase-2 is distinct from the cyclooxygenase-1 which has also been cloned, sequenced and characterized from sheep, murine and human sources. Cyclooxygenase-2 is rapidly and readily inducible by a number of agents including mitogens, endotoxin, hormones, cytokines and growth factors. Given that prostaglandins have both physiological and pathological roles, we have concluded that the constitutive enzyme, cyclooxygenase-1, is responsible for much of the endogenous basal release of prostaglandins and hence is important in their physiological functions which include the maintenance of gastrointestinal integrity and renal blood flow. In contrast the inducible form of the enzyme, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties of a conventional non-steroidal antiinflammatory drug (NSAID), will inhibit hormone-induced uterine contractions and will have potential anti-cancer effects, but will also have a diminished ability to induce some of the mechanism-based side effects. In particular, such a selective inhibitor should have a reduced potential for gastrointestinal toxicity, a reduced potential for renal side effects, a reduced effect on bleeding times and possibly a reduced ability to induce asthma attacks in aspirin-sensitive asthmatic subjects.

Accordingly, it is an object of this invention to provide assays and materials to identify and evaluate pharmacological agents that are potent inhibitors of cyclooxygenase-2 and cyclooxygenase-2 activity.

It is also an object of this invention to provide assays and materials to identify and evaluate pharmacological agents that preferentially or selectively inhibit cyclooxygenase-2 and cyclooxygenase-2 activity over cyclooxygenase-1 and cyclooxygenase-1 activity.

BRIEF DESCRIPTION OF THE DRAWINGS

FIGS. 1A–1C Full length amino acid sequence of a human cyclooxygenase-2 protein (SEQ.ID.NO:18).

FIGS. 2A–2C Full length nucleotide sequence of a cloned human cyclooxygenase-2 complementary DNA obtained from human osteosarcoma cells (SEQ.ID.NO:19).

FIGS. 3. 749 base flanking sequence for human cyclooxygenase-1 complementary DNA obtained from plasmid pcDNA-1-hCOX-1 (SEQ.ID.NO.13).

SUMMARY OF THE INVENTION

The invention encompasses a system for high level expression of human cyclooxygenase-2 protein including a high expression human cyclooxygenase-2 (COX-2) cDNA and mammalian expression vectors.

The invention also encompasses assays to identify and evaluate pharmacological agents that are potent inhibitors of cyclooxygenase-2 and cyclooxygenase-2 activity. The invention further encompasses assays to identify and evaluate pharmacological agents that preferentially or selectively inhibit cyclooxygenase-2 and cyclooxygenase-2 activity over cyclooxygenase-1 and cyclooxygenase-1 activity.

The invention also encompasses recombinant DNA molecules wherein the nucleotide sequence encoding human cyclooxygenase-2 protein is attached to the 3' flanking sequence of the gene encoding human cyclooxygenase-1, expression vectors containing COX-2/COX-1 nucleotide sequence fusions and systems for enhanced expression of human cyclooxygenase-2 protein.

DETAILED DESCRIPTION OF THE INVENTION

In one embodiment the invention encompasses an assay for determining the cyclooxygenase-2 activity of a sample comprising the steps of:
(a) adding
(1) a human osteosarcoma cell preparation,
(2) a sample, the sample comprising a putative cyclooxygenase-2 inhibitor, and
(3) arachidonic acid; and
(b) determining the amount of prostaglandin $E_2$ produced in step (a).

For purposes of this specification human osteosarcoma cells are intended to include, but are not limited to commercially available human osteosarcoma cell lines, such as those available from the American Type Culture Collection (ATCC) Rockville, Md. such as osteosarcoma 143B (ATTC CRL 8303) and osteosarcoma 143B PML BK TK (ATCC CRL 8304). We have found osteosarcoma 143.98.2, which was originally obtained from Dr. William Sugden, McArdle Laboratory for Cancer Research, University of Wisconsin-Madlison, to be useful. We have now made a Budapest Treaty deposit of osteosarcoma 143.98.2 with ATCC on Dec. 22, 1992 under the identification Human osteosarcoma 143.98.2 (now ATCC CRL 11226).

For purposes of this specification the osteosarcoma cell preparation shall be defined as an aqueous monolayer or suspension of human osteosarcoma cells, a portion of which will catalyze the synthesis of prostaglandin $E_2$ ($PGE_2$). Furthermore the preparation contains a buffer such as HANK'S balanced salt solution.

Within this embodiment is the genus where the human osteosarcoma cells are from the osteosarcoma 143 family of cell types which include osteosarcoma 143B and 143B PML BK TK. We have used osteosarcoma 143.98.2.

For purposes of this specification the osteosarcoma cell preparation also includes human osteosarcoma microsomes, a portion of which will catalyze the synthesis of $PGE_2$. The microsomes may be obtained as described below from any of the osteosarcoma cell lines herein disclosed.

A second embodiment the invention encompasses a composition comprising
  (a) an osteosarcoma cell preparation, having between approximately $10^3$ and approximately $10^9$ osteosarcoma cells per ml of cell preparation, and
  (b) 0.1 to 50 µl of peroxide-free arachidonic acid per mL of cell preparation.

Typically the cell preparation will be grown as a monolayer and used in an aliquot of $8.2\times10^4$ to $2\times10^6$ cells per well (of approximately 1 mL working volume) as described in the protocol below. Arachidonic acid is typically used in amounts of 1 to 20 µl per well of approximately 1 mL working volume.

When osteosarcoma microsomes are used instead of whole cells, the cell preparation will typically comprise 50 to 500 µg of microsomal protein per mnL of cell preparation. Arachidonic acid is typically used in amounts of 1 to 20 µl acid per mnL of cell preparation.

A third embodiment the invention encompasses an assay for determining the cyclooxygenase-1 activity of a sample comprising the steps of:
  (a) adding
    (1) a cell preparation, the cells expressing cyclooxygenase-1 but not expressing cyclooxygenase-2,
    (2) a sample, the sample comprising a putative cyclooxygenase-1 inhibitor,
    (3) arachidonic acid; and
  (b) determining the amount of $PGE_2$ produced in step (a).

For purposes of tllis specification cells capable of expressing cyclooxygenase-1 but incapable of expressing cyclooxygenase-2, include human histiocytic lymphoma cells such as U-937 (ATCC CRL 1593). Such cells are hereinafter described as COX-1 cells.

For purposes of this specification the cell preparation shall be defined as an aqueous suspension of cells, typically at a concentration of $8\times10^5$ to $1\times10^7$ cells/ml. The suspension will contain a buffer as defined above.

A fourth embodiment of the invention encompasses a human cyclooxygenase-2 which is shown in FIG. 1 This cyclooxygenase-2 is also identified as SEQ.ID.NO:18. At page 5, lines 24–27, replace the existing paragraph with the following:

A fifth embodiment of the invention encompasses a human cyclooxygenase-2 (COX-2) cDNA which is shown in FIG. 2 or a degenerate variation thereof. This cyclooxygenase-2 cDnNA is also identified as SEQ.ID.NO:19.

Within this embodiment is the reading frame portion of the sequence shown in FIG. 2 encoding the cyclooxygenase-2 shown in FIG. 1; the portion being bases 97 through 1909.

As will be appreciated by those of skill in the art, there is a substantial amount of redundancy in the codons which are translated to specific amino acids. Accordingly, the invention also includes alternative base sequences wherein a codon (or codons) are replaced with another codon, such that the amino acid sequence translated by the DNA sequence remains unchanged. For purposes of this specification, a sequence bearing one or more such replaced codons will be defined as a degenerate variation. Also included are mutations (changes of individual amino acids) which produce no significant effect in the expressed protein.

A sixth embodiment of the invention encompasses a system for stable expression of cyclooxygenase-2 as shown in FIG. 2 or a degenerate variation thereof comprising:
  (a) an expression vector such as vaccinia expression vector pTM 1, baculovirus expression vector pJVETLZ, pUL941 and pAcmP1 INVITROGEN vectors pCEP4 and pcDNAI; and
  (b) a base sequence encoding human cyclooxygenase-2 as shown in FIG. 2 or a degenerate variation thereof.

In one genus of this embodiment cyclooxygenase-2 is expressed in Sf9 or Sf21 cells (INVITROGEN).

A seventh embodiment of the invention encompasses a human cyclooxygenase-2 cDNA useful for high level expression of cyclooxygenase-2.

Within this embodiment the invention comprises the human cyclooxygenase-2 protein-coding open reading frame cDNA sequence, bases 97 to 1909 in FIG. 2, and the human cyclooxygenase-1 flanking region, bases 1 to 749 of FIG. 3, the flanking region being attached to the 3' end of the human cyclooxygensase-2 cDNA.

An eighth embodiment the invention encompasses a system for enhanced stable expression of human cyclooxygenase-2 comprising: (a) an expression vector such as vaccinia expression vector pTM1, baculovirus expression vector pJVETLZ, pUL941 and pAcmP1 INVITROGEN vectors pCEP4 and pcDNAI; and (b) a base sequence encoding human cyclooxygenase-2 as shown in FIG. 2 or a degenerate variation thereof.

In one genus of this embodiment cyclooxygenase-2 is expressed in Sf9 or Sf21 cells (INVITROGEN).

A variety of mammalian expression vectors may be used to express recombinant cyclooxygenase-2 in mammalian cells. Commercially available mammalian expression vectors which may be suitable for recombinant cyclooxygenase-2 expression include but are not limited to pMClneo (Stratagene), pXTI (Stratagene), pSG5 (Stratagene), EBO-pSV2-neo (ATCC 37593), pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and gZD35 (ATCC 37565).

DNA encoding cyclooxygenase-2 may also be cloned into an expression vector for expression in a recombinant host cell. Recombinant host cells may be prokaryotic or eukaryotic and include but are not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are clonally propagated and individually analyzed to determine whether they produce cyclooxygenase-2 protein. Identification of cyclooxygenase-2 expressing host cell clones may be done by several means, including but not limited to immunological reactivity with anti-cyclooxygenase-2 antibodies, and the presence of host cell-associated cyclooxygenase-2 activity.

Expression of cyclooxygenase-2 DNA may also be performed using in vitro produced synthetic mRNA. Synthetic mRNA can be efficiently translated in various cell-free systems, including but not limited to wheat germ extracts and reticulocyte extracts. Synthetic mRNA can also be efficiently translated in cell-based systems, including but not limited to microinjection into oocytes, with microinjection into frog oocytes being preferred.

To determine the cyclooxygenase-2 cDNA sequence(s) that yields optimal levels of enzymatic activity and/or cyclooxygenase-2 protein, cyclooxygenase-2 cDNA molecules including but not limited to the following can be constructed: the full-length open reading frame of the cyclooxygenase-2 cDNA (base 97 to base 1909 as shown in FIG. 2). All constructs can be designed to contain none, all or portions of the 3' untranslated region of cyclooxygenase-2 cDNA (bases 1910–3387).

Cyclooxygenase-2 activity and levels of expression can be determined following the introduction, both singly and in combination, of these constructs into appropriate host cells. Following determination of the cyclooxygenase-2 cDNA cassette yielding optimal expression in transient assays, this cyclooxygenase-2 cDNA construct is transferred to a variety of expression vectors, including but not limited to mammalian cells, baculovirus-infected insect cells, bacteria such as *Escherichia coli*, and yeast such as *Saccharomyces cerevisiae*.

Mammalian cell transfectants, insect cells and microinjected oocytes are assayed for the levels of cyclooxygenase-2 activity and levels of cyclooxygenase-2 protein by the following methods.

One method for measuring cyclooxygenase-2 enzymatic activity involves the incubation of the cells in the presence of 20 µM arachidonic acid for 10 minutes and measurement of $PGE_2$ production by EIA.

A second method involves the direct measurement of cyclooxygenase-2 activity in cellular lysates or microsomes prepared from mammalian cells transfected with cyclooxygenase-2 cDNA or oocytes injected with cyclooxygenase-2 mRNA. This assay is performed by adding arachidonic acid to lysates and measuring the $PGE_2$ production by EIA.

Levels of cyclooxygenase-2 protein in host cells are quantitated by immunoaffinity and/or ligand affinity techniques. Cyclooxygenase-2 specific affinity beads or cyclooxygenase-2 specific antibodies are used to isolate $^{35}S$-methionine labelled or unlabelled cyclooxygenase-2 protein. Labelled cyclooxygenase-2 protein is analyzed by SDS-PAGE and/or Western blotting. Unlabelled cyclooxygenase-2 protein is detected by Western blotting, ELISA or RIA assays employing cyclooxygenase-2 specific antibodies.

Following expression of cyclooxygenase-2 in a recombinant host cell, cyclooxygenase-2 protein may be recovered to provide cyclooxygenase-2 in active form, capable of participating in the production of $PGE_2$. Several cyclooxygenase-2 purification procedures are available and suitable for use. As described above for purification of cyclooxygenase-2 from natural sources, recombinant cyclooxygenase-2 may be purified from cell lysates and extracts, by various combinations of, or individual application of salt fractionation, ion exchange chromatography, size exclusion chromatography, hydroxylapatite adsorption chromatography and hydrophobic interaction chromatography.

In addition, recombinant cyclooxygenase-2 can be separated from other cellular proteins by use of an immunoaffinity column made with monoclonal or polyclonal antibodies specific for full length nascent cyclooxygenase-2.

Whole Cell Assays

For the cyclooxygenase-2 and cyclooxygenase-1 assays, human osteosarcoma cells were cultured and used in aliquots of typically 8×104 to 2×10$^6$ cells/well. We have found it convenient to culture the cells in 1 ml of media in 24-well multidishes (NUNCLON) until they are confluent. The number of cells per assay may be determined from replicate plates prior to assays, using standard procedures. Prior to the assay, the cells are washed with a suitable buffer such as Hank's Balanced Salts Solution (HBSS; SIGMA), which is preferably prewarmed to 37° C. Approximately 0.5 to 2 ml is added per well.

Prior to assay, the appropriate number of COX-1 cells ($10^5$ to $10^7$ cells/ml) are removed from cultures and concentrated using a technique such as by centrifugation at 300×g for 10 minutes. The supernatant is decanted and cells are washed in a suitable buffer. Preferably, cells are again concentrated, such as by centrifugation at 300×.g. for 10 minutes, and resuspended to a fmal cell density of approximately $1.5×10^6$ cells/ml, preferably in prewarmed HBSS.

Following incubation of human osteosarcoma cells or COX-1 cells in a suitable buffer, a test compound and/or vehicle samples (such as DMSO) is added, and the resulting composition gently mixed. Preferably the assay is performed in triplicate. Arachidonic acid is then added in proportions as described above. We prefer to incubate the cells for approximately 5 minutes at 30 to 40° C., prior to the addition of the of peroxide-free arachidonic acid (CAYMAN) diluted in a suitable buffer such as HBSS. Control samples should contain ethanol or other vehicle instead of arachidonic acid. A total reaction incubation time of 5 to 10 minutes at to 37° C. has proven satisfactory. For osteosarcoma cells, reactions may be stopped by the addition HCl or other acid, preferably combined with mixing, or by the rapid removal of media directly from cell monolayers. For U-937 cells, reactions may be advantageously be performed in multiwell dishes or microcentrifuge tubes and stopped by the addition of HCl or another mineral acid. Typically, samples assayed in 24-multidishes are then transferred to microcentrifuge tubes, and all samples frozen on dry ice. Similarly, samples are typically stored at −20° C. or below prior to analysis of $PGE_2$ levels.

Quantitation of PGE) Concentrations

Stored osteosarcoma 143 and U-937 samples are thawed, if frozen, and neutralized, if stored in acid. Samples are then preferably mixed, such as by vortexing, and $PGE_2$ levels measured using a $PGE_2$ enzyme immunoassay, such as is commercially available from CAYMAN. We have advantageously conducted the plating, washing and color development steps as an automated sequence using a BIOMEK 1000 (BECKMAN). In the preferred procedure, following the addition of ELLMANS reagent, color development is monitored at 415 nm using the BIORAD model 3550 microplate reader with MICROPLATE MANAGER/PC DATA ANALYSIS software. Levels of $PGE_2$ are calculated from the standard curve, and may optionally determined using BECKMAN IMMlNOFIT EIARIA analysis software.

In the absence of the addition of exogenous arachidonic acid, levels of $PGE_2$ in samples from both human osteosarcoma cells and COX-1 cells are approximately typically 0.1 to 2.0 ng/10$^6$ cells. In the presence of arachidonic acid, levels of $PGE_2$ increased to approximately 5 to 10 fold in osteosarcoma cells and 50 to 100 fold in COX-1 cells. For purposes of this specification, cellular cyclooxygenase activity in each cell line is defined as the difference between $PGE_2$ levels in samples incubated in the absence or presence of arachidonic acid, with the level of detection being approximately 10 pg/sample. Inhibition of $PGE_2$ synthesis by test compounds is calculated between $PGE_2$ levels in samples incubated in the absence or presence of arachidonic acid.

Microsomal Cyclooxygenase Assay

Human osteosarcoma cells may be grown and maintained in culture as described above. Approximately $10^5$ to $10^7$ cells are plated in tissue culture plates such as available from NUNCLON and maintained in culture for 2 to 7 days. Cells may be washed with a suitable buffer such phosphate buffered saline, JIBS), pH 7.2. Cells are then removed from the plate, preferably by scraping into PBS. Samples may then be concentrated, such as by centrifuging at 400×g for 10 minutes at 4° C. Cell pellets or other concentrates are either stored at a suitable reduced temperature such as −80° C., or processed immediately. All further manipulations of the cells are preferably performed at 0–4° C. Cell pellets or concentrates obtained from two tissue culture plates are resuspended in a standard protective buffer, such as Tris-Cl, pH 7.4, containing 10 mM ethylene diaminetetraacetic acid (EDTA), 1 mM phenylmethylsulfonylfluoride, 2 µg/ml leupeptin, 2 µg/ml aprotinin, and 2 µg/ml soybean trypsin inhibitor and blended or homogenized, such as by sonication for three×5 seconds using a 4710 series ultrasonic homogenizer (COLE-PARMER) set at 75% duly cycle, power level 3. Enriched microsomal preparations are then prepared, such as by differential centrifugation to yield an enriched microsomal preparation. In our preferred procedure, the first step consists of four sequential centrifugations of the cell homogenate at 10,000×g for 10 min at 4° C. After each centrifugation at 10,000×g the supernatant is retained and recentrifuged. Following the fourth centrifugation, the supernatant is centrifuged at 100,000×g for 60–90 min at 4° C. to pellet the microsomal fraction. The 100,000×g supernatant is discarded, and the 100,000×g microsomal pellet is resuspended in a suitable buffer such as 0.1 M Tris-Cl, pH 7.4, containing 10 mM EDTA and 0.25 mg/ml delipidized bovine serum albumin (BSA) (COLLABORAITIVE RESEARCH INCORPORATED). The resulting microsomal suspension is recentrifuged such as at 100,000×g for 90 min at 4° C. to recover the microsomes. Following this centrifugation the microsomal pellet is resuspended in a stabilizing buffer, such as 0.1 M Tris-Cl, pH 7.4, containing 10 mM EDTA at a protein concentration of approximately 2–5 mg/ml. Aliquots of osteosarcoma microsomal preparations may be stored at low temperature, such as at −80° C. and thawed prior to use.

As may be appreciated by those of skill in the art, human or serum albumin or other albumin, may be used as an alternative to BSA. Applicants have found that while the procedure may be carried out using standard BSA or other albumin, delipidized BSA is preferred. By use of delipidized BSA, endogenous microsomal arachidonic acid can be reduced by a factor of at least 2, such that the arachidonic acid produced in the assay constituted at least 90% of the total. As may be appreciated by those of skill in the art, other lipid adsorbing or sequestering agents may also be used. For purposes of this specification microsomes from which the exogenous arachidonic acid has been reduced by a factor of approximately 2 or more shall be considered to be microsomes that are substantially free of exogenous arachidonic acid.

COX-1 cells are grown and maintained in culture as described above, washed in a suitable buffer, such as PBS, and cell pellets or concentrates stored, preferably at −80° C. Cell pellets or concentrates corresponding to approximately $10^9$ to $10^{10}$ cells were resuspended in a suitable buffer, such as 10 ml of 0.1 M Tris-HCl, pH 7.4, and are then blended or homogenized, such as by sonication for 2×5 seconds and 1×10 seconds using a 4710 series ultrasonic homogenizer (COLE-PARMER) set at 75% duty cycle, power level 3. The cell homogenate is then concentrated and resuspended. In our preferred procedure the cell homogenate is centrifuged at 10,000×g for 10 minutes at 4° C. The supernatant fraction is then recentrifuged at 100,000×g for 2 hours at 4° C., and the resulting microsomal pellet resuspended in a suitable buffer, such as 0.1 M Tris-HCl, 1 mM EDTA, pH 7.4 to a protein concentration of approximately 1 to 10 mg/ml. Aliquots of osteosarcoma microsomal preparations may be stored at reduced temperature and thawed prior to use.

Assay Procedure

Microsomal preparations from Human osteosarcoma and U937 cells are diluted in buffer, such as 0.1 M Tris-HCl, 10 mM EDTA, pH 7.4, (Buffer A) to a protein concentration of 50 to 500 µg/ml. 10 to 50 µl of test compound or DMSO or other vehicle is added to 2 to 50 µl of buffer A. 50 to 500 µl of microsomes suspension is then added, preferably followed by mixing and incubation for 5 minutes at room temperature. Typically, assays are performed in either duplicate or triplicate. Peroxide-free arachidonic acid (CAYMAN) in Buffer A is then added to a final concentration of 20 µM arachidonic acid, followed by incubation, preferably at room temperature for 10 to 60 minutes. Control samples contained ethanol or other vehicle instead of arachidonic acid. Following incubation, the reaction was terminated by addition of HCl or other mineral acid. Prior to analysis of $PGE_2$ levels, samples were neutralized. Levels of $PGE_2$ in samples may be quantitated as described for the whole cell cyclooxygenase assay.

Cyclooxygenase activity in the absence of test compounds was determined as the difference between $PGE_2$ levels in samples incubated in the presence of arachidonic acid or ethanol vehicle, and reported as ng of $PGE_2$/mg protein. Inhibition of $PGE_2$ synthesis by test compounds is calculated between $PGE_2$ levels in samples incubated in the absence or presence of arachidonic acid.

EXAMPLE 1

Whole Cell Cyclooxygenase Assays

Human osteosarcoma 143.98.2 cells were cultured in DULBECCOS MODIFIED EAGLES MEDIUM (SIGMA) containing 3.7 g/l $NaHCO_3$ (SIGMA), 100 µg/l gentamicin (GIBCO), 25 mM HEPES, pH 7.4 (SIGMA), 100 IU/ml penicillin (FLOW LABS), 100 jg/ml streptomycin (FLOW LABS), 2 mM glutamine (FLOW LABS) and 10% fetal bovine serum (GIBCO). Cells were maintained at 37° C., 6% $CO_2$ in $150cm^2$ tissue culture flasks (CORNING). For routine subculturing, media was removed from confluent cultures of cells, which were then incubated with 0.25% trypsin/0.1 % EDTA (JRH BIOSCIENCES) and incubated at room temperature for approximately 5 minutes. The trypsin solution was then aspirated, and cells resuspended in fresh medium and dispensed at a ratio of 1:10 or 1:20 into new flasks.

U-937 cells (ATC° C. CRL 1593) were cultured in 89% RPMI-1640 (SIGMA), 10% fetal bovine serum (GIBCO), containing 50 lU/ml penicillin (Flow labs), 50 µg/ml streptomycin (FLOW LABS) and 2 g/l $NaHCO_3$ (SIGMA). Cells were maintained at a density of $0.1-2.0 \times 10^6$/ml in 1 liter spinner flasks (Coming) at 37° C., 6% $CO_2$. For routine subculturing, cells were diluted in fresh medium and transferred to fresh flasks.

Assay Protocol

For cyclooxygenase assays, osteosarcoma 143.98.2 cells were cultured in 1 ml of media in 24-well multidishes (NUNCLON) until confluent. The number of cells per assay was determined from replicate plates prior to assays, using standard procedures. Immediately prior to cyclooxygenase assays, media was aspirated from cells, and the cells washed once with 2 ml of Hanks balanced salts solution (HBSS; SIGMA) prewarmed to 37° C. 1 ml of prewarmed HBSS was then added per well.

Immediately prior to cyclooxygenase assays, the appropriate number of U-937 cells were removed from spinner cultures and centrifuged at 300×g for 10 minutes. The supernatant was decanted and cells washed in 50 ml of HBSS prewarmed to 37° C. Cells were again pelleted at 300×g for 10 minutes and resuspended in prewarmed HBSS to a final cell density of approximately $1.5 \times 10^6$ cells/ml. 1 ml aliquots of cell suspension were transferred to 1.5 ml microcentrifuge tubes or 24-well multidishes (Nunclon).

Following washing and resuspension of osteosarcoma 143 and U-937 cells in 1 ml of HBSS, 1 μl of test compounds or DMSO vehicle were added, and samples gently mixed. All assays were performed in triplicate. Samples were then incubated for 5 minutes at 37° C., prior to the addition of 10 μl of peroxide-free arachidonic acid (CAYMAN) diluted to 1 μM in HBSS. Control samples contained ethanol vehicle instead of arachidonic acid. Samples were again gently mixed and incubated for a further 10 minutes at 37° C. For osteosarcoma cells, reactions were then stopped by the addition of 100 μl of 1N HCl, with mixing, or by the rapid removal of media directly from cell monolayers. For U-937 cells, reactions in multiwell dishes or microcentrifuge tubes were stopped by the addition of 100 μl of 1N HCl, with mixing. Samples assayed in 24-multidishes were then transferred to microcentrifuge tubes, and all samples were frozen on dry ice. Samples were stored at −20° C. prior to analysis of $PGE_2$ levels.

Quantitation of $PGE_2$ Concentrations

Osteosarcoma 143.98.2 and U-937 samples were thawed, and 100 μl of 1N NaOH added to samples to which 1N HCl had been added prior to freezing. Samples were then mixed by vortexing, and $PGE_2$ levels measured using a $PGE_2$ enzyme immunoassay (CAYMAN) according to the manufacturers instructions. The plating, washing and colour development steps of this procedure were automated using a BIOMEK 1000 (BECKMAN). Following the addition of ELLNLkNS reagent, color development was monitored at 415 nm using the Biorad model 3550 microplate reader with microplate manager/PC data analysis software. Levels of $PGE_2$ were calculated from the standard curve determined using BECKMAN IMMUNOFIT EIA/RIA analysis software.

Results

In the absence of the addition of exogenous arachidonic acid, levels of $PGE_2$ in samples from both osteosarcoma 143 cells and U-937 cells were generally 2 ng/$10^6$ cells. In the presence of arachidonic acid, levels of $PGE_2$ in samples from these cell lines increased to approximately 5 to 10 fold in osteosarcoma cells and 50 to 100 fold in U-937 cells.

Table 1 show the effects of a series of non-steroidal antiinflammatory compounds on $PGE_2$ synthesis by human osteosarcoma 143 cells and U-937 cells in response to exogenous arachidonic acid.

TABLE 1

| SAMPLE | CONCENTRATION nM | osteosarcoma 143 $PGE_2$ ng/$10^6$ cells | U-937 $PGE_2$ |
|---|---|---|---|
| -AA | — | 1.8 | 0.15 |
| AA, no inhibitor | — | 8.6 | 17.7 |
| NS-389 | 100.0 | 0.8 | 18.9 |
|  | 30.0 | 1.1 | 17.7 |
|  | 10.0 | 3.0 | 20.4 |
|  | 3.0 | 2.7 | 18.3 |
|  | 1.0 | 3.2 | 17.7 |
|  | 0.3 | 8.3 | 18.3 |
| ibuprofen | 100,000 | 2.5 | 1.1 |
|  | 10,000 | 5.7 | 5.5 |
|  | 1,000 | 5.4 | 14.3 |
|  | 300 | 10.8 | 15.8 |
|  | 100 | 12.8 | 17.1 |
|  | 10 | 12.5 | 16.4 |

EXAMPLE 2

Microsomal Cyclooxygenase Assay

Osteosarcoma 143.98.2 cells were grown and maintained in culture as described above. $3 \times 10^6$ cells were plated in 245×245×20 mm tissue culture plates (NUNCLON) and maintained in culture for 5 days. Cells were washed twice with 100 ml of phosphate buffered saline, pH 7.2, (PBS) and then scraped from the plate with a sterile rubber scraper into PBS. Samples were then centrifuged at 400×g for 10 minutes at 4° C. Cell pellets were either stored at −80° C. until use or processed immediately. All further manipulations of the cells were performed at 0–4° C. Cell pellets obtained from two tissue culture plates were resuspended in 5 ml of 0.1 M Tris-Cl, pH 7.4, containing 10 mM EDTA, 1 mM phenylmethylsulfonylfluoride, 2 μg/ml leupeptin, 2 μg/ml aprotinin, and 2 μg/ml soybean trypsin inhibitor and sonicated for three×5 seconds using a 4710 series ultrasonic homogenizer (Cole-Parmer) set at 75% duty cycle, power level 3. The cell homogenates were then subjected to a differential centrifugation protocol to yield an enriched microsomal preparation. The first step consisted of four sequential centrifugations of the cell homogenate at 10,000×g for 10 min at 4° C. After each centrifugation at 10,000×g the supernatant was retained and recentrifuged. Following the fourth centrifugation, the supernatant was centrifuged at 100,000×g for 60–90 min at 4° C. to pellet the microsomal fraction. The 100,000×g supernatant was discarded and the 100,000×g microsomal pellet was resuspended in 8 mls of 0.1 M Tris-Cl, pH 7.4, containing 10 mM EDTA and 0.25 mg/ml delipidized bovine serum albumin (COLLABORATIVE RESEARCH INCORPORATED). The resulting microsomal suspension was recentrifuged at 100,000×g for 90 min at 4° C. to recover the microsomes. Following this centrifugation the microsomal pellet was resuspended in 0.1 M Tris-Cl, pH 7.4, containing 10 mM EDTA at a protein concentration of approximately 2–5 mg/ml. 500 t aliquots of osteosarcoma microsomal preparations were stored at −80° C. and thawed on ice immediately prior to use.

U-937 cells were grown and maintained in culture as described above, washed in PBS, and cell pellets frozen at −80° C. Cell pellets corresponding to approximately $4 \times 10^9$ cells were resuspended in 10 ml of 0.1 M Tris-HCl, pH 7.4 and sonicated for 2×5 seconds and 1×10 seconds using a 4710 series ultrasonic homogenizer (COLE-PARMER) set at 75% duty cycle, power level 3. The cell homogenate was then centrifuged at 10,000×g for 10 minutes at 4° C. The supernatant fraction was then recentrifuged at 100,000×g for 2 hours at 4° C., and the resulting microsomal pellet resuspended in 0.1 M Tris-HCl, 1 mM EDTA, pH 7.4 to a protein concentration of approximately 4 mg/ml. 500 µl aliquots of osteosarcoma microsomal preparations were stored at −80° C. and thawed on ice immediately prior to use.

Assay Protocol

Microsomal preparations from osteosarcoma 143 and U-937 cells were diluted in 0.1 M Tris-HCl, 10 mM EDTA, pH 7.4, (buffer A) to a protein concentration of 100 µg/ml. All subsequent assay steps, including the dilution of stock solutions of test compounds, were automated using the BIC)MEK 100 (BIORAD). 5 µl of test compound or DMSO vehicle was added, with mixing, to 20 µl of buffer A in a 96-well minitube plate (BECKMAN). 200 µl of microsomes suspension was then added, followed by mixing and incubation for 5 minutes at room temperature. Assays were performed in either duplicate or triplicate. 25 µl of peroxide-free arachidonic acid (CAYMAN) in buffer A is then added to a final concentration of 20 µM aracidonic acid, with mixing, followed by incubation at room temperature for 40 minutes. Control samples contained ethanol vehicle instead of arachidonic acid. Following the incubation period, the reaction was terminated by the addition of 25 µl of IN HCl, with mixing. Prior to analysis of $PGE_2$ levels, samples were neutralized by the addition of 25 µl of 1 N NaOH. Levels of $PGE_2$ in samples were quantitated by enzyme immunoassay (CAYMAN) as described for the whole cell cyclooxygenase assay. The results are shown in Table II.

TABLE II

MICROSOMAL ASSAY RESULTS - SET 1

| DRUG | 143.98.2 % Inhibition | U-937 % Inhibition |
| --- | --- | --- |
| 100 nM DuP-697 | 92 | 6 |
| 3 uM DuP-697 | 93 | 48 |
| 100 nM Flufenamic | 16 | 5 |
| 3 uM Flufenamic | 36 | 0 |
| 100 nM Flosulide | 13 | 0 |
| 3 uM Flosulide | 57 | 0 |
| 100 nM Zomipirac | 45 | 30 |
| 3 uM Zomipirac | 66 | 67 |
| 100 nM NS-398 | 45 | 0 |
| 3 uM NS-398 | 64 | 0 |
| 100 nM Diclofenac | 70 | 49 |
| 3 uM Diclofenac | 86 | 58 |
| 100 nM Sulindac sulfide | 19 | 0 |
| 3 uM Sulindac sulfide | 33 | 4 |
| 100 nM FK-3311 | 20 | 0 |
| 3 uM FK-3311 | 26 | 0 |
| 100 nM Fluribprofen | 55 | 57 |
| 3 uM Fluribprofen | 58 | 89 |

EXAMPLE 3

Reverse Transcriptase/Polymeirase Chain Reaction

In order to confirm the type of cyclooxygenase mRNA present in osteosarcoma 143.38.2 cells, a reverse transcriptase polymerase chain reaction (RT-PCR) analytical technique was employed. Total RNA was prepared from osteosarcoma cells harvested 1–2 days after the cultures had reached confluence. The cell pellet was resuspended in 6 ml of 5 M guanidine monothiocyanate containing 10 mM EDTA, 50 mM Tris-Cl, pH 7.4, and 8% (w/v) β-mercaptoethanol. The RNA was selectively precipitated by addition of 42 ml of 4 M LiCl, incubation of the solution for 16 h at 4° C., followed by recovery of the RNA by centrifugation at 10,000×g for 90 min at 4° C. The RNA pellet which was obtained was resuspended in 10 mM Tris-HCl, pH 7.5, 1 mM EDTA, and 0.1 % SDS at a concentration of 4 µg/ml and used directly for quantitation of COX-1 and COX-2 mRNAs by RT-PCR.

The quantitative RT-PCR technique employs pairs of synthetic oligonucleotides which will specifically amplify cDNA fragments from either COX-1 or COX-2, or the control mRNA, glyceraldehyde-3-phosphate-dehydrogenase (G3PDH). The synthetic oligonucleotides are described in Maier, Hla, and Maciag (*J. Biol. Chem.* 265: 10805–10808 (1990)); Hla and Maciag (*J. Biol. Chem.* 266: 24059–24063 (1991)); and Hla and Neilson (*Proc. Natl. Acad. Sci.*, (*USA*) 89: 7384–7388 (1992)), and were synthesized according to the following sequences:

Human COX-1 specific oligonucleotides

5'-TGCCCAGCTCCTGGCCCGCCGCTT-3' SEQ. ID. NO:1:

5'-GTGCATCAACACAGGCGCCTCTTC-3' SEQ. ID. NO:2:

Human COX-2 specific oligonucleotides

5'-TTCAAATGAGATTGTGGGAAAATTGCT-3' SEQ. ID. NO:3:

5'-AGATCATCTCTGCCTGAGTATCTT-3' SEQ. ID. NO:4:

Human glyceraldehyde-3-phosphate dehydrogenase specific oligonucleotides

5'-CCACCCATGGCAAA1TCCATGGCA-3' SEQ. ID. NO:5:

5'-TCTAGACGGCAGGTCAGGTCCACC-3' SEQ. ID. NO:6:

The RT-PCR reactions were carried out using a RT-PCR kit from CETUS-PERKIN ELMER according to the manufacturers instructions. Briefly, 4 µg of osteosarcoma total RNA was reverse transcribed to cDNA using reverse transcriptase and random hexamers as primers for 10 min at 23° C., 10 min at 42° C., followed by an incubation at 99° C. for 5 min. The osteosarcoma cDNA sample was split into three equal aliquots which were amplified by PCR using 10 pmol of specific oligonucleotide pairs for either COX-1 or COX-2, or G3PDH. The PCR cycling program was 94° C. for 1 min, 55° C. for 1 min, and 72° C. for 1 min. After the twentieth, twenty-fifth, and thirtieth cycle an aliquot was removed from the reaction mixture and stopped by the addition of 5 mM EDTA. Control reactions included RT-PCR reactions which contained no RNA and also reactions containing RNA but no reverse transcriptase.

Following RT-PCR the reactions were electrophoresed through a 1.2 % agarose gel using a Tris-sodium acetate-EDTA buffer system at 110 volts. The positions of PCR-generated DNA fragments were determined by first staining the gel with ethidium bromide. The identity of the amplified DNA fragments as COX-1, COX-2, or G3PDH was confirmed by Southern blotting, using standard procedures. Nitrocellulose membranes were hybridized with radiolabelled COX-1, COX-2, or G3PDH-specific probes. Hybridization of the probes was detected by autoradiography and also by determining the bound radioactivity by cutting strips of the nitrocellulose which were then counted by liquid scintillation counting.

The RT-PCRISouthern hybridization experiment demonstrated that COX-2 mRNA is easily detected in osteosarcoma cell total RNA. No COX-1 cDNA fragment could be generated by PCR from osteosarcoma cell total RNA, although other mRNA species such as that for G3PDH are detected. These results demonstrate that at the sensitivity level of RT-PCR, osteosarcoma cells express COX-2 mRNA but not COX-1 mRNA.

Western Blot of U-937 and 143.98.2 Cell RNA

We have developed a rabbit polyclonal antipeptide antiserum (designated MF-169) to a thyroglobulin-conjugate of a peptide corresponding to amino acids 589–600, inclusive, of human cyclooxygenase-2. This amino acid sequence:

Asp-Asp-Ile-Asn-Pro-Thr-Val-Leu-Leu-Lys-Glu-Arg. (also identified herein as SEQ. ID. NO:7:) has no similarity to any peptide sequence of human cyclooxygenase-1. At a dilution of 1:150, this antiserum detects by immunoblot a protein corresponding to the molecular weight of cyclooxygenase-2 in microsomal preparations from osteosarcoma 143 cells. The immunoblot procedure used for these studies has previously been described (Reid et al., *J. Biol. Chem.* 265: 19818–19823 (1990)). No band corresponding to the molecular weight of cyclooxygenase-2 is observed using a 1:150 dilution of pre-immune serum from the rabbit used to raise antiserum. Furthermore, a band corresponding to the molecular weight of cyclooxygenase-2 is observed by immunoblot in microsomal preparations of osteosarcoma 143 cells using a 1:1 50 dilution of a commercially available polyclonal antiserum against cyclooxygenase-2 (CAYMAN). This antiserum is reported to not cross-react with cyclooxygenase-1. These results demonstrate that osteosarcoma 143 cells express cyclooxygenase-2. Furthermore, immunoblot analysis with these antisera and northern blot analysis using a COX-2-specific probe demonstrated that levels of cyclooxygenase-2 protein and the corresponding mRNA increase in osteosarcoma 143 cells as they grow past confluence. Within a 3-hour period, and in the presence of 1% serum, human recombinant IL1-α (10 pg/ml; R and D systems Inc.) human recombinant IL1-β (10 pg/ml; R and D systems Inc.), human EGF (15 ng/ml; CALBIOCHEM) and conditioned medium from cells grown beyond confluence also increased levels of $PGE_2$ synthesis by osteosarcoma 143 cells in response to arachidonic acid, relative to cells grown in the absence of these factors.

EXAMPLE 4

Identification by Northern Blot Analysis of Cell Lines Expressing Either cox-1 or cox-2 Exclusively Northern blot analysis was used to determine that U-937 cells express only COX-1 mRNA whereas osteosarcoma 143.98.2 expresses only COX-2 mDNA This was accomplished by first cloning human Cox-2 cDNA from total RNA of the human 143 osteosarcoma cell line. Total RNA was prepared from approximately $1\times10^8$ 143 osteosarcoma cells using 4M guanidinium isothiocyanate (Maniatis, et al., (1982) *Molecular Cloning*, Cold Spring Harbor). Oligonucleotide primers corresponding to the 5' and 3' ends of the published Cox-2 cDNA sequence (Hla and Neilson, (1992) *Proc. Natl. Acad. Sci., USA* 89, 7384–7388) were prepared and are shown below.

HCOX-1 5'CTGCGATGCTCGCCCGCGCCCTG3' 5'Primer

HCOX-2 5'CTTCTACAGTTCAGTCGAACGTTC3' 3'Primer

These primers (also identified hereinunder as SEQ. ID. NO:8: and SEQ. ID. NO:9: respectively) were used in a reverse transcriptase PCR reaction of 143 osteosarcoma total RNA. The reaction contained 1 μg of 143 osteosarcoma total RNA, which was first reverse transcribed using random hexamers and reverse transcriptase (Maniatis, et al., (1982) *Molecular Cloning*, Cold Spring Harbor). The products from this reaction were then amplified using the HCOX-1 and HCOX-2 primers described above and Taq polymerase (Saiki, et al., (1988) *Science*, 239, 487–488). The conditions used for the amplification were 94° C. for 30 sec, 55° C. for 30 sec and 72° C. for 2 min 15 sec for 30 cycles. The amplified products were run on a 1% low melt agarose gel and the 1.9 kb DNA fragment corresponding to the predicted size of human COX-2 cDNA was excised and recovered. An aliquot of the recovered COX-2 cDNA was reamplified as described above (no reverse transcriptase reaction), the amplified products were again run on a 1% low melt agarose gel and recovered.

By standard procedures as taught in Maniatis, et al., (1982) *Molecular Cloning*, Cold Spring Harbor, this 1.9 kb DNA fragment was cloned into the Eco RV site of pBluescript KS (obtained from STRATAGENE) and transformed into competent DH5a bacteria (obtained from BRL) and colonies selected on LB agar/ampicillan overnight. Three clones giving the correct Pst I and Hinc II restriction digestions for human COX-2 cDNA were sequenced completely and verified to be correct. This was the first indication that the human 143 osteosacoma cell line expressed COX-2 mRNA.

Northern Analysis

Total RNA from various cell lines and tissues were prepared using the guanidinium isothiocyanate method as described above (Maniatis, et al., (1982) *Molecular Cloning*, Cold Spring Harbor). Poly A+ RNA was prepared using oligo dT cellulose spin columns (Maniatis, et al., (1982) *Molecular Cloning*, Cold Spring Harbor). The RNA, 10 μg of total or 5 μg of U937 Poly A+ were electrophoresed on 0.9% agarose 2.2 M formaldehyde gels (Maniatis, et al., (1982) *Molecular Cloning*, Cold Spring Harbor). After electrophoresis the gel was washed 3 times for 10 minutes each with distilled water and then two times for 30 minutes each in 10×SSC (1×SSC=0.15 M NaCl and 0.015 m sodium citrate). The RNA was transferred to nitrocellulose using capillary transfer (Maniatis, et al., (1982) *Molecular Cloning*, Cold Spring Harbor) overnight in 10×SSC. The next day the filter was baked in a vacuum oven at 80° C. for 1.5 hrs to fix the RNA onto the nitrocellulose. The filter was then equilibriated in pre-hybridization buffer (50% formamide, 6×SSC, 50 mM sodium phosphate buffer pH 6.5, 10 ×Denhardts solution, 0.2% SDS and 250 μg/ml of sheared and denatured salmon sperm DNA) for approximately 4 hours at 40° C. The COX-2 cDNA probe was prepared using $^{32}$p dCTP and random hexamer priming with T7 DNA, polymerase using a commercial kit (Pharmacia). Hybridization was carried out using the same buffer as for pre-hybridization plus $1-3\times10^6$ cpmlml of denatured COX-2 cDNA probe at 40° C. overnight. The blots were washed two times in 1×SSC and 0.5% SDS at 50° C. for 30 minutes each, wrapped in Saran Wrap and exposed to Kodak XAR film with screen at −70° C. for 1–3 days. The same blots were stripped of COX-2 probe by putting them in boiling water and letting it cool to room temperature. The blot was re-exposed to film to ensure all hybridization signal was removed and then pre-hybridized and hybridized as described above using human COX-1 cDNA as probe. The human COX-1 cDNA was obtained from Dr. Colin Funk, Vanderbilt University, however the sequence is known in the art (See Funk, C. D., Ftmk, L. B., Kennedy, M. E., Pong, A. S., and Fitzgerald, G. A. (1991), *FASEBJ*, 5 pp 2304–2312).

Using this Northern blot procedure applicants have established that the human 143 osteosarcoma cell line RNA hybridized only to the Cox-2 probe and not to the Cox-1 probe. The size of the hybridizing band obtained with the Cox-2 probe corresponded to the correct size of Cox-2 mRNA (approximately 4 kb) suggesting that 143 osteosarcoma cells only express Cox-2 mRNA and no Cox-1 mRNA. This has been confirmed by RT-PCR as described above.

Similarly, the human cell line U937 Poly A+ RNA hybridized only to the Cox-1 probe and not to the Cox-2 probe. The hybridizing signal corresponded to the correct size for Cox-1 mRNA (approximately 2.8 kb) suggesting that U937 only express Cox-1 MnRNA and not Cox-2. This was also confirmed by RT-PCR, since no product was obtained from U937 Poly A+ RNA when Cox-2 primers were used (see above).

EXAMPLE 5

Human Cyclooxygenase-2 cDNA and Assays for Evaluating Cyclooxygenase-2 Activity Examples demonstrating expression of the Cox -2 cDNA Comparison of the Cox-2 cDNA sequence obtained by RT-CR of human osteosarcoma total RNA to the published sequence (Hia, eilson 1992 *Proc. Natl. Acad. Sci. USA*, 89, 7384–7388), revealed a ase change in the second position of codon 165. In the published sequence codon 165 is GGA, coding for the amino acid glycine, whereas in the osteosarcoma Cox-2 cDNA it is GAA coding for the amino acid glutamic acid.

To prove that osteosarcoma Cox-2 cDNA codes for glutanic acid at position 165 we repeated RT-PCR amplification of osteosarcoma Cox-2 mRNA; amplified, cloned and sequenced the region surrounding this base change from human genomic DNA; and used site directed mutagenesis to change Cox-2glu165 to Cox-2gly165 and compared there activities after transfection into COS-7 cells.

1. RT-PCR of Cox-2 mRNA from Human Osteosarcoma Total RNA.

A 300bp Cox-2 cDNA fragment that includes codon 165 was amplified by RT-PCR using human osteosarcoma 143 total RNA. Two primers:

Hcox-13 5'CCTTCCTTCGAAATGCAATTA3'
SEQ.ID.NO:10

Hcox-14 5'AAACTGATGCGTGAAGTGCTG3'
SEQ.ID.NO:11 were prepared that spanned this region and were used in the PCR reaction. Briefly, cDNA was prepared from 1 µg of osteosarcoma 143 total RNA, using random priming and reverse transcriptase (Maniatis et al., 1982, *Molecular Cloning*, Cold Spring Harbor). This cDNA was then used as a template for amplification using the Hcox-13 and Hcox-14 primers and Taq polymerase (Saki, et al., 1988, *Science*, 238, 487–488). The reaction conditions used were, 94° C. for 30s, 52° C. for 30s and 72° C. for 30s, for 30 cycles. After electrophoresis of the reaction on a 2% low melt agarose gel, the expected 300 bp amplified product was obtained, excised from the gel and recovered from the agarose by melting, phenol extraction and ethanol precipitation. The 300 bp fragment was ligated into the TAII cloning vector (Invitrogen) and transformed into *E. Coli* (INVαF) (Invitrogen). Colonies were obtained and 5 clones were picked at random which contained the 300 bp insert and sequenced. The sequence of codon 165 for all 5 clones was GAA (glutarmic acid). Since the DNA sequence amplified was only 300 bp and the Taq polymerase has quite high fidelity for amplification of smaller fragments and its the second amplification reaction in which GAA was obtained for codron 165 confirms that Cox-2 geRNA from osteosarcoma has GAA for codon 165.

2. Amplificati on of Cox-2 Codon 165 Region from Genomic DNA.

To confirm that the osteosarcoma Cox-2 sequence was not an artefact of the osteosarcoma cell line and that this sequence was present in normal cells, the DNA sequences containing codon 165 was amplified from human genomic DNA prepared from normal blood.

The primers used for the amplification reaction were Hcox-13 and Hcox-14. The genoic organization of the human Cox-2 gene has not yet been determined. Using mouse Cox-2 gene organization as a model for the exon-intron positioning of the human Cox-2 gene would place primer Hcox-13 in exon 3 and Hcox-14 in exon 5. The size of the amplified product would be around 2000 bp based on the mouse Cox-2 gene organization. The PCR reaction contained 1 µg of human genomic DNA, Hcox-13 and Hcox-14 primers and Taq polymerase. The reaction conditions used were 94° C. for 30s, 52° C. for 30s and 72° C. for 45s, for 35 cycles. An aliquot of the reaction products was separated on a 1% low melt agarose gel. Th ere were however a number of reaction products and to identify the correct fragment, the DNA was transferred to a nylon membrane by southern blotting and probed with a P-32 labelled human Cox-2 internal oligo.

Hcox-17 5'GAGATTGTGGGAAAATTGCTT3'
SEQ.ID.NO:12

Hybridization was to a 1.4 kb DNA frag ment which was recovered from the remainder of the PCR reaction by electrophoresis on a 0.8% low melt agarose gel as described above. This fragment was ligated into the TAII cloning vector (Invitrogen) and used to transform bacteria (as described above). A clone contailnng this insert was recovered and sequenced. The sequence at codon 165 was Gwe (glutaonic acid) and this sequence was from the human Cox-2 gene since the coding region was interrupted by introns. (Th e 3' splice site of intron 4 in human is the same as the mouse). This is very convincing evidence of the existence of a human Cox-2 having glutagic acid at position 165.

3. Cox-2gnlu65 vs Cox-2gly65 Activity in Transfected Cos-7 Cells

To determine if Cox-2glul 65 has cyclooxygenase activity and to compare its activity to Cox-2gly165, both cDNA sequences were cloned into the eukaryotic expression vector pcDNA-1 (Invitrogen) and itransfected into COS-7 cells (see below). Activity was determined 48h after transfection by incubating the cells with 20 µM arachadonic acid and measuring $PGE_2$ production by EIA (Cayman). The Cox-2gly165 sequence was obtained by site directed mutagenesis of Cox-2glu165. Briefly, single stranted KS+ plasmid (Stratagene) DNA containing were Cox-2glu165 sequence cloned into the Eco RV site of the multiple cloning region was prepared by adding 1ml of an overnight bacterial culture (XL-1 Blue (Stratagene) containing the COX-2 plasmid) to 100 ml of LB ampicillian (100 µg/ml) and grown at 37° C. for 1 hr. One ml of helper phage, M13K07, (Pharmacia) was then added and the culture incubated for an additional 7 hrs. The bacteria were pelleted by centrifugation at 10,000×g for 10 min, ¼ volume of 20% PEG, 3.5 M ammonium acetate was added to the supernatant and the phage precipitated overnight at 4° C. The single stranded phage were recovered the next day by centrifugation at 17,000×g for 15 min, after an additional PEG precipitation the single stranded DNA was prepared from the phage by phenol and phenol:chloroform extractions and ethanol precipitation. The single stranded DNA containing the Cox-2glu165 sequence was used as template for site directed mutagenesis using the T7-GEN in vitro mutagenesis kit from U.S. Biochemical. The single stranded DNA (1.6 pmoles) was annealed to the phosphorylated oligo HCox-17 (16 pmoles), which changes codon 165 from GAA to GGA and the second strand synthesis carried out in the presence of 5-Methyl-dC plus the other standard deoxynucleoside triphosphates, T7 DNA polymerase and T4 DNA ligase. After synthesis the parental strand was nicked using the restriction endonuclease Msp 1 and then removed by exonuclease ImI digestion. The methylated mutated strand was rescued by transformation of *E. coli* mcAB-. Colonies were picked, sequenced and a number of clones were obtained that now had GGA for codon 165 instead of GAA. This Cox-2gly165 sequence was released from the bluescript KS vector by an Eco R1-Hind III digestion, recovered and cloned into the eukaryotic expression vector pcDNA-1 (Invitrogen) which had also been digested with Eco R1-Hind III. The Cox-2glu165 sequence was also cloned into the pcDNA-1 vector in the exact same manner. The only difference between the two plasmids was the single base change in codon 165.

The COX-2 pcDNA-1 plasmids were used to transfect Cos-7 cells using a modified calcium phospate procedure as described by Chen and Okyama (Chen, C. A. and Okyama, H. 1988. *Biotechniques*, 6, 632–638). Briefly, $5\times10^5$ Cos-7 cells were plated in a 10 cm culture dish containing 10 ml media. The following day one hour before transfection the media was changed. The plasmid DNA (1–30 μl) was mixed with 0.5 ml of 00.25 M $CACl_2$ and 0.5 ml of 2×BBS (50 mM N-, N-Bis(2-hydroxethyl)-2-amino-ethanesulfonic acid, 280 mM NaCl, 1.5 mM $Na_2HPO_4$) and incubated at room temperature for 20 min. The mixture was then added dropwise to the cells with swirling of the plate and incubated overnight (15–18 hrs) at 35° C. in a 3% $CO_2$ incubator. The next day the media was removed, the cells washed with PBS, 10 ml of fresh media added and the cells incubated for a further 48 hrs at 5% $CO_2$–37° C.

The cells were transfected with 2.5, 5 or 10 μg of Cox-2glu165/pcDNA-1 or Cox-2gly165/PcDNA-1. Two plates were used for each DNA concentration and as a control the cells were transfected with pcDNA-1 plasmid. After 48 hours the medium was removed from the cells, the plates were washed 3× with Hank's media and then 2 ml of Hank's media containing 20 μM arachadonic acid was added to the cells. After a 20 min incubation at 37° C. the medium was removed from the plate and the amount of $PGE_2$ released into the medium was measured by EIA. The $PGE_2$ EIA was performed using a commercially available kit (Caymen) following the manufacturers instructions. Shown in Table III the amount of $PGE_2$ released into the media from COS7 cells transfected with pcDNA-1, COS7 transfected with Cox-2glu165/pcDNA-1 and COS7 transfected with Cox-2gly165/pcDNA-1. Depending on the amount of DNA transfected into the COS7 cells, Cox-2glu165 is 1.3 to 2.3 times more active than Cox-2gly165.

TABLE III

| LEVEL OF $PGE_2$ (PG/ML) RELEASED FROM TRANSFECTED COS-7 CELLS | | | |
|---|---|---|---|
| | $PGE_2$ pg/ml | | |
| Amount of Transfected DNA (μg) | 2.5 | 5.0 | 10.0 |
| Cos-7 + COX-2glu165/pcDNA1 | 1120 | 2090 | 4020 |
| Cos-7 + COX-2gly165/pcDNA1 | 850 | 1280 | 1770 |
| Cos-7 or Cos-7 + pcDNA1 (5 μg) < 3.9 pg/ml $PGE_2$ | | | |

EXAMPLE 6

Vaccinia Virus-directed High Level Expression of Human COX-2 in Mammalian Cells Requires a 3' Non-protein Coding Flanking Sequence Human COX-2glu165 cDNA was recombined into vaccinia virus using the vaccinia virus transfer vector pTM1 (Moss, et al., (1990) *Nature*, 348, 91–92). Two recombinant vaccinia viruses containing human COX-2 were constructed. The first vaccinia virus construct, termed vv-hCOX2-orf, contained only the open reaching frame cDNA sequence coding for the COX-2 protein. The second vaccinia virus construct, termed vv-hcox-2-3'fl, contained the COX-2 protein-coding open reading frame cDNA sequence and the human COX-1 non-coding 3'flanking region attached to the 3' end of the COX-2 coding sequence.

The human COX-1 non-coding 3' flanking region as the following sequence: (SEQ.ID.NO:13)

```
  1 GGGGC AGGAAAGCAG CATTCTGGAG GGGAGAGCTT TGTGCTTGTC
 46 ATTCCAGAGT GCTGAGGCCA GGGCTGATGG TCTTAAATGC TCATTTTCTG
 96 GTTTGGCATG GTGAGTGTTG GGGTTGACAT TTAGAACTTT AAGTCTCACC
146 CATTATCTGG AATATTGTGA TTCTGTTTAT TCTTCCAGAA TGCTGAACTC
196 CTTGTTAGCC CTTCAGATTG TTAGGAGTGG TTCTCATTTG GTCTGCCAGA
246 ATACTGGGTT CTTAGTTGAC AACCTAGAAT GTCAGATTTC TGGTTGATTT
296 GTAACACAGT CATTCTAGGA TGTGGAGCTA CTGATGAAAT CTGCTAGAAA
346 GTTAGGGGGT TCTTATTTTG CATTCCAGAA TCTTGACTTT CTGATTGGTG
396 ATTCAAAGTG TTGTGTTCCC TGGCTGATGA TCCAGAACAG TGGCTCGTAT
446 CCCAAATCTG TCAGCATCTG GCTGTCTAGA ATGTGGATTT GATTCATTTT
496 CCTGTTCAGT GAGATATCAT AGAGACGGAG ATCCTAAGGT CCAACAAGAA
546 TGCATTCCCT GAATCTGTGC CTGCACTGAG AGGGCAAGGA AGTGGGGTGT
596 TCTTCTTGGG ACCCCCACTA AGACCCTGGT CTGAGGATGT AGAGAGAACA
646 GGTGGGCTGT ATTCACGCCA TTGGTTGGAA GCTACCAGAG CTCTATCCCC
696 ATCCAGGTCT TGACTCATGG CAGCTGTTTC TCATGAAGCT AATAAAATTC
746 GCCC
```

The relative abilities of these recombinant vaccinate viruses direct COX-2 expression in infected COS7 cells were determined by assaying COX activity in microsomes isolated from infected cells. Microsomes were prepared from cells infected for 24 hours with either vv-hCOX2-orf and vv-hcox-2-3'fl. Low levels of COX-2 expression in a mammalian cell line occurred when cells were infected with only the open reading frame of COX-2 (vv-hCOX2-orf). Higher levels of COX-2 expression were achieved when human COX-1 non-coding 3' flanking region was attached to the 3' end of the COX-2 open reading frame sequence (vv-hcox-2-3'fl).

The vv-hCOX2-orf construct contained only the COX-2 protein-coding open reading frame cDNA sequence encoded by the base sequence 97 to 1912 as shown in FIG. 2. The ATG methionine start codon of the COX-2 cDNA (bases 97–99, FIG. 2) was precisely fused to the ATG methionine start codon provided by the NcoI restriction site of pTM1 (Moss, et al., supra) using the complementary synthetic oligonucleotides GO148 and GO149.

GO148 is

5'-CATGCTCGCCCGCGCCCTGCTGCTGTGCGCGGT CCTGGCGT-3' (SEQ.ID.NO:14)

GO149 is

5'-CAGGACCGCGCACAGCAGCAGGGCGCGGGCG AG-3' (SEQ.ID.NO:15)

The annealed oligonucleotides GO148/GO349 en code a modified NcoI site spanning an ATG nethionine start codon, the first 14 codons of COX-2 FIG. 2; Met-Leu-Ala-Arg-Ala-Leu-Leu-Leu-Cys-Ala-Val-Leu-Ala (SEQ.ID.NO:20)), the first nucleotide of the fifteenth codon of COX-2 (Leu), and an HaeII restriction enzyme site encoded by the last five nucleotides of oligonucleotide GO148. A human COX-2 cDNA fragment (FIG. 2, bases 133 to 1912) was prepared by digesting plastd pKS-hCOX-2glu165 with the restriction enzymes HaeII and BamHI to yeild a 1.9 kilobase pair DNA fragment encoding amino acids 14 to 604 of human COX-2 (FIG. 1). The annealed oligonucleotides GO148/GO149 and the HaeII-BamHI human COX-2 cDNA fragment were ligated into the vaccinia transfer vector PTM1 between the Ncol and BamHI restriction sites to create plasmid pTM1hCOX2-orf.

The vv-hcox-2-3'fl construct contained the COX-2 protein- coding open reading frame cDNA sequence and the human COX-1 non-coding 3' flanking region; the 5' end of the human COX-1 sequence was attached to the 3' end of the COX-2 coding sequence. The human COX-1 non-coding 3' flanking region was prepared by polymerase chain reaction (PCR) amplification using the plasmid pcDNA-hCOX-1 as a template (Funk, et al., (1991) *FASEB J.*, 5, 2304–2312). The oligonucleotides used for amplification of the human COX-1 3' flanking sequence are:

GO156 is

5'-CTAGCTAGCTAGAATTCGGGGCAGGAAAGCAG CATTCT-3' (SEQ.ID.NO:16)

GO157 is

5'-TCGATCGATCGAGGATCCGGGCGAATTTTATTA GCTTCA-3' (SEQ.ID.NO:17)

Oligonucleotidc GO156 contains an 11 nucleotide clamp sequence (i.e., 5'-CTAGCTAGCTA-3' (SEQ.ID.NO:21)), an EcoRI restriction site (i.e., 5'-GAATTC-3'), followed by the first 21 nucleotides (i.e., 5'-GGGGCAGGAAAGCAGCATTCT-3' (SEQ.ID.NO:22)) after the TGA stop codon in the human COX-1 cDNA sequence (Funk, et al., (1991) *FASEB J.*, 5, 2304–2312; see FIG. 3, bases 1–21). Oligonucleotide GO157 contains a 12 nucleotide clamp sequence (i.e., 5'-TCGATCGATCGA-3' (SEQ.ID.NO:23)), a BamHI restriction site (i.e., 5'-GGATCC-3') and a 21 nucleotide sequence complementary to the last 21 nucleotides of the human COX-1 cDNA sequence (Funk, et al., (1991) *FASEB J.*, 5, 2304–2312; see FIG. 3, bases 728–749).

The PCR reaction was carried out using a PCR kit from CETUS-PERKIN ELMER according to the manufacturers instructions. Briefly, 1 pg of plasmid pcDNA-hCOX-1 (Funk, et al., (1991) *FASEB J.*, 5, 2304–2312) was used as a template for PCR amplification by Taq DNA polymerase in the presence of 50 picomoles of oligonucleotides GO156 and GO157. The PCR cycling program was 94° C. for 1 min, 55° C. for 1 min, and 72° C. for 1 min for 32 cycles. The 784 base pair fragment generated by the PCR was digested with BamHI and EcoRI restriction enzymes to remove the clamp sequences. The resulting 749 base pair DNA fragment was ligated to the 3' coding end of human COX-2 in the plasmid pTM1hCOX2-orf, which had previously been cleaved with EcoRI and BamHI, to create plasmid pTM1-hCOX2-3'fl.

Recombinant vaccinia virus containing human COX-2 sequences were generated according to the standard protocols outlined by Ausubel et al., (*Current Protocols in Molecular Biology*, 2, pp 16.15.1–16.19.9, Wiley & Sons, New York). Plasmids pTM1-hCOX2-orf and pTM1-hCOX23'fl were recombined into vaccinia virus at the thymidine kinase locus by homologous recombination. The homologous recombination was carried out by first infecting approximately $1\times10^6$ COS-7 cells with $5\times10^5$ plaque forming units (pfu) of wild type vaccinia virus (Western Reserve strain) for 2 hours at 37° C. Two hours post-infection the cells were then transfected with 5 to 10 µg of the plasmid DNAs pTM1-hCOX2-orf and pTM1-hCOX2-3'fl. The transfection was carried out using a calcium phosphate mammalian transfection kit according to the manufacturer's instructions (STRATAGENE). A calcium phosphate precipitate of the plasmid DNAs pTM1-hCOX2-orf and pTM1-hCOX2-3'fl was prepared by mixing 5 to 10 µg of DNA in 450 µl $H_2O$ with 50 µl of 2.5 M $CaCl_2$ and 500 µl of 2×N,N-bis (2-hydroxyethyl)-2-aminoethanesulfconic acid in buffered saline. The resulting $CaPO_4$-DNA precipitate was layered onto the vaccinia virus infected-COS7 cells for 4 hours, removed by aspiration and replaced with fresh medium. The virally-infected and plasmid-transfected COS7 cells were incubated for 2 days at 37° C., harvested by scraping, and disrupted by sonication. The transfected cell lysate was used to select and screen recombinant virus plaques.

Selection and screening of recombinant virus plaques were carried out in HuTK-143B cells (ATCC CRL8303) using thymidine kinase selection. Briefly, dilutions of COS7 cell lysates from cells co-transfected with wild-type vaccinia virus and either plasmid pTM1hCOX2-orf or plasmid pTM1-hCOX2-3'fl were plated onto confluent monolayers of HuTK-143B cells grown in the presence of 25 µg/ml of bromodeoxyuridine. Under these conditions viral plaques result only from vaccinia virus that have undergone a recombination event at the thymidine kinase locus leading to an inactive thymidine kinase gene product. A fraction of the recombinant viruses will result from homologous recombination of the hCOX-2 cDNA sequences in pTM1-hCOX2orf and pTM1-hCOX2-3'fl into the vaccinia virus thymidine kinase locus.

Recombinant vaccinia viruses containing hCOX-2 sequences were isolated by standard selection and screening procedures as outlined by Ausubel et al., (supra). Briefly, recombinant vaccinia viruses were detected by dot-blot hybridization using radioactively labelled DNA probes generated from human COX-1 and COX-2 DNA sequences.

Following three rounds of plaque purification and amplification, two recombinant vaccinia viruses (vv-hCOX2-orf and vv-hCOX2-3'fl) were generated. Both of these viruses contain the entire human COX-2 protein-coding cDNA sequence located downstream from a T7 DNA polymerase promoter sequence integrated into the thymidine kinase locus of vaccinia virus. The construct vv-hCOX2-3'fl also contains the 3' noncoding flanking region of human COX-1 appended to the 3' end of the COX-2 gene.

The ability of vv-hCOX2-orf and vv-hCOX2-3'fl to direct the expression of COX-2 expression was determined by assaying COX-2 activity in COS7 cells that had been infected with vaccinia virus constructs. COS7 cells were grown and maintained in culture as described above. COS7 cells were grown to a cell density of approximately $1\times10^7$ cells in a 175 cm$^2$ tissue culture flask in 40 ml of medium and then infected with vaccinia virus at a multiplicity-of-infection of 10:1. Three different infections were carried out: (a) a control infection using approximately $10^8$ plaque forming units (pfu) of the helper virus vT7-3 (Moss, et al., (1990) *Nature*, 348, 91–92) for each 175 cm$^2$ tissue culture flask; (b) a test infection using approximately $10^8$ pfu of the helper virus vT73 and approximately $10^8$ pfu of vv-hCOX2-orf for each 175 cm$^2$ tissue culture flask; and (c) a test infection using approximately $10^8$ pfu of the helper virus vT7-3 and about $10^8$ pfu of vv-hCOX2-3'fl for each 175 cm$^2$ tissue culture flask. The infections were carried out at 37° C. for 24 hours and were followed by cell harvesting and preparation of microsomes as described above. The COX activity in the microsomal fractions was assayed by determining the level of de novo PGE$_2$ synthesis from arachidonic acid as described above. Briefly, each microsomal assay contained 25 µg of microsomal protein in a total volume of 200 µl of 100 mM Tris-OH, pH 7.4, 10 mM EDTA. The reaction was initiated by the addition of arachidonic acid to a fmal concentration of 20 µM followed by incubation at 23° C. for 40 min. The levels of PGE$_2$ in samples were quantitated by enzyme immunoassay (CAYMAN) or radioimmunoassay (NEW ENGLAND NUCLEAR) as described above for the whole cell cyclooxygenase assay. For comparison, the levels of COX-2 activity as determined by PGE$_2$ synthesis in microsomes prepared from osteosarcoma 143B cells and assayed as described above, is presented in Table IV.

TABLE IV

MICROSOMAL ASSAY RESULTS OF COX EXPRESSION IN COS-7 CELLS INFECTED WITH VACCINIA VIRUS CONTAINING HUMAN COX-2 CDNA'S

| CELL SOURCE FOR MICROSOME PREPARATION | VACCINIA VIRUS | CYCLOOXYGENASE ACTIVITY ng PGE$_2$ synthesized/mg microsomal protein | |
|---|---|---|---|
| | | −arachidonic acid | +arachidonic acid |
| Osteosarcoma 143 | none | 5 | 20 |
| COS-7 | vT7-3 | 0.12 | 0.37 |
| COS-7 | vT7-3 + vv-hCOX2-orf | 2.1 | 14 |
| COS-7 | vT7-3 + vv-hCOX2-3'fl | 92.5 | 3,300 |

What is claimed is:

1. An isolated DNA fragment consisting of SEQ.ID.NO:13.

\* \* \* \* \*

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

TGCCCAGCTC CTGGCCCGCC GCTT    24

(2) INFORMATION FOR SEQ ID NO: 2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

GTGCATCAAC ACAGGCGCCT CTTC    24

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

TTCAAATGAG ATTGTGGGAA AATTGCT                                              27

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

AGATCATCTC TGCCTGAGTA TCTT                                                 24

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

CCACCCATGG CAAATTCCAT GGCA                                                 24

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

TCTAGACGGC AGGTCAGGTC CACC                                                 24

(2) INFORMATION FOR SEQ ID NO: 7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Asp Asp Ile Asn Pro Thr Val Leu Leu Lys Glu Arg
 1               5                  10

(2) INFORMATION FOR SEQ ID NO: 8:

(i) SEQUENCE CHARACTERISTICS:
        (A) LENGTH: 23 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

CTGCGATGCT CGCCCGCGCC CTG                                                23

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

CTTCTACAGT TCAGTCGAAC GTTC                                               24

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

CCTTCCTTCG AAATGCAATT A                                                  21

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

AAACTGATGC GTGAAGTGCT G                                                  21

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GAGATTGTGG GAAAATTGCT T                                                  21

(2) INFORMATION FOR SEQ ID NO: 13:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 13:

```
GGGGCAGGAA AGCAGCATTC TGGAGGGGAG AGCTTTGTGC TTGTCATTCC AGAGTGCTGA      60
GGCCAGGGCT GATGGTCTTA AATGCTCATT TTCTGGTTTG GCATGGTGAG TGTTGGGGTT     120
GACATTTAGA ACTTTAAGTC TCACCCATTA TCTGGAATAT TGTGATTCTG TTTATTCTTC     180
CAGAATGCTG AACTCCTTGT TAGCCCTTCA GATTGTTAGG AGTGGTTCTC ATTTGGTCTG     240
CCAGAATACT GGGTTCTTAG TTGACAACCT AGAATGTCAG ATTTCTGGTT GATTTGTAAC     300
ACAGTCATTC TAGGATGTGG AGCTACTGAT GAAATCTGCT AGAAAGTTAG GGGGTTCTTA     360
TTTTGCATTC CAGAATCTTG ACTTTCTGAT TGGTGATTCA AAGTGTTGTG TTCCCTGGCT     420
GATGATCCAG AACAGTGGCT CGTATCCCAA ATCTGTCAGC ATCTGGCTGT CTAGAATGTG     480
GATTTGATTC ATTTTCCTGT TCAGTGAGAT ATCATAGAGA CGGAGATCCT AAGGTCCAAC     540
AAGAATGCAT TCCCTGAATC TGTGCCTGCA CTGAGAGGGC AAGGAAGTGG GGTGTTCTTC     600
TTGGGACCCC CACTAAGACC CTGGTCTGAG GATGTAGAGA GAACAGGTGG GCTGTATTCA     660
CGCCATTGGT TGGAAGCTAC CAGAGCTCTA TCCCCATCCA GGTCTTGACT CATGGCAGCT     720
GTTTCTCATG AAGCTAATAA AATTCGCCC                                      749
```

(2) INFORMATION FOR SEQ ID NO: 14:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

```
CATGCTCGCC CGCGCCCTGC TGCTGTGCGC GGTCCTGGCG C                         41
```

(2) INFORMATION FOR SEQ ID NO: 15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

```
CAGGACCGCG CACAGCAGCA GGGCGCGGGC GAG                                  33
```

(2) INFORMATION FOR SEQ ID NO: 16:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

```
CTAGCTAGCT AGAATTCGGG GCAGGAAAGC AGCATTCT                             38
```

(2) INFORMATION FOR SEQ ID NO: 17:

(i) SEQUENCE CHARACTERISTICS:

(A) LENGTH: 39 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 17:

TCGATCGATC GAGGATCCGG GCGAATTTTA TTAGCTTCA                                39

(2) INFORMATION FOR SEQ ID NO: 18:

(i) SEQUENCE CHARACTERISTICS:
            (A) LENGTH: 604 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 18:

```
Met Leu Ala Arg Ala Leu Leu Cys Ala Val Leu Ala Leu Ser His
 1               5                  10                  15

Thr Ala Asn Pro Cys Cys Ser His Pro Cys Gln Asn Arg Gly Val Cys
                20                  25                  30

Met Ser Val Gly Phe Asp Gln Tyr Lys Cys Asp Cys Thr Arg Thr Gly
             35                  40                  45

Phe Tyr Gly Glu Asn Cys Ser Thr Pro Glu Phe Leu Thr Arg Ile Lys
         50                  55                  60

Leu Phe Leu Lys Pro Thr Pro Asn Thr Val His Tyr Ile Leu Thr His
 65                  70                  75                  80

Phe Lys Gly Phe Trp Asn Val Val Asn Asn Ile Pro Phe Leu Arg Asn
                 85                  90                  95

Ala Ile Met Ser Tyr Val Leu Thr Ser Arg Ser His Leu Ile Asp Ser
                100                 105                 110

Pro Pro Thr Tyr Asn Ala Asp Tyr Gly Tyr Lys Ser Trp Glu Ala Phe
            115                 120                 125

Ser Asn Leu Ser Tyr Tyr Thr Arg Ala Leu Pro Pro Val Pro Asp Asp
        130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
```

-continued

```
            290                 295                 300
Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
                340                 345                 350

Phe Asn Lys Gln Phe Gln Tyr Gln Asn Arg Ile Ala Ala Glu Phe Asn
                355                 360                 365

Thr Leu Tyr His Trp His Pro Leu Leu Pro Asp Thr Phe Gln Ile His
370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
                420                 425                 430

Val Ser Gln Ala Ser Ile Asp Gln Ser Arg Gln Met Lys Tyr Gln Ser
                435                 440                 445

Phe Asn Glu Tyr Arg Lys Arg Phe Met Leu Lys Pro Tyr Glu Ser Phe
450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
                500                 505                 510

Ala Pro Phe Ser Leu Lys Gly Leu Met Gly Asn Val Ile Cys Ser Pro
                515                 520                 525

Ala Tyr Trp Lys Pro Ser Thr Phe Gly Gly Glu Val Gly Phe Gln Ile
                530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
                580                 585                 590

Pro Thr Val Leu Leu Lys Glu Arg Ser Thr Glu Leu
                595                 600
```

(2) INFORMATION FOR SEQ ID NO: 19:

(i) SEQUENCE CHARACTERISTICS:
        (A) LENGTH: 3387 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

```
GTCCAGGAAC TCCTCAGCAG CGCCTCCTTC AGCTCCACAG CCAGACGCCC TCAGACAGCA      60

AAGCCTACCC CCGCGCCGCG CCCTGCCCGC CGCTCGGATG CTCGCCCGCG CCCTGCTGCT     120

GTGCGCGGTC CTGGCGCTCA GCCATACAGC AAATCCTTGC TGTTCCCACC CATGTCAAAA     180

CCGAGGTGTA TGTATGAGTG TGGGATTTGA CCAGTATAAG TGCGATTGTA CCCGGACAGG     240
```

```
ATTCTATGGA GAAAACTGCT CAACACCGGA ATTTTTGACA GAATAAAAT TATTTCTGAA      300

ACCCACTCCA AACACAGTGC ACTACATACT TACCCACTTC AAGGGATTTT GGAACGTTGT      360

GAATAACATT CCCTTCCTTC GAAATGCAAT TATGAGTTAT GTCTTGACAT CCAGATCACA      420

TTTGATTGAC AGTCCACCAA CTTACAATGC TGACTATGGC TACAAAAGCT GGGAAGCCTT      480

CTCTAACCTC TCCTATTATA CTAGAGCCCT TCCTCCTGTG CCTGATGATT GCCCGACTCC      540

CTTGGGTGTC AAAGGTAAAA AGCAGCTTCC TGATTCAAAT GAGATTGTGG AAAAATTGCT      600

TCTAAGAAGA AAGTTCATCC CTGATCCCCA GGGCTCAAAC ATGATGTTTG CATTCTTTGC      660

CCAGCACTTC ACGCATCAGT TTTTCAAGAC AGATCATAAG CGAGGGCCAG CTTTCACCAA      720

CGGGCTGGGC CATGGGGTGG ACTTAAATCA TATTTACGGT GAAACTCTGG CTAGACAGCG      780

TAAACTGCGC CTTTTCAAGG ATGGAAAAAT GAAATATCAG ATAATTGATG GAGAGATGTA      840

TCCTCCCACA GTCAAAGATA CTCAGGCAGA GATGATCTAC CCTCCTCAAG TCCCTGAGCA      900

TCTACGGTTT GCTGTGGGGC AGGAGGTCTT TGGTCTGGTG CCTGGTCTGA TGATGTATGC      960

CACAATCTGG CTGCGGGAAC ACAACAGAGT ATGCGATGTG CTTAAACAGG AGCATCCTGA     1020

ATGGGGTGAT GAGCAGTTGT TCCAGACAAG CAGGCTAATA CTGATAGGAG AGACTATTAA     1080

GATTGTGATT GAAGATTATG TGCAACACTT GAGTGGCTAT CACTTCAAAC TGAAATTTGA     1140

CCCAGAACTA CTTTTCAACA AACAATTCCA GTACCAAAAT CGTATTGCTG CTGAATTTAA     1200

CACCCTCTAT CACTGGCATC CCCTTCTGCC TGACACCTTT CAAATTCATG ACCAGAAATA     1260

CAACTATCAA CAGTTTATCT ACAACAACTC TATATTGCTG GAACATGGAA TTACCCAGTT     1320

TGTTGAATCA TTCACCAGGC AAATTGCTGG CAGGGTTGCT GGTGGTAGGA ATGTTCCACC     1380

CGCAGTACAG AAAGTATCAC AGGCTTCCAT TGACCAGAGC AGGCAGATGA ATACCAGTC     1440

TTTTAATGAG TACCGCAAAC GCTTTATGCT GAAGCCCTAT GAATCATTTG AAGAACTTAC     1500

AGGAGAAAAG GAAATGTCTG CAGAGTTGGA AGCACTCTAT GGTGACATCG ATGCTGTGGA     1560

GCTGTATCCT GCCCTTCTGG TAGAAAAGCC TCGGCCAGAT GCCATCTTTG GTGAAACCAT     1620

GGTAGAAGTT GGAGCACCAT TCTCCTTGAA AGGACTTATG GGTAATGTTA TATGTTCTCC     1680

TGCCTACTGG AAGCCAAGCA CTTTTGGTGG AGAAGTGGGT TTTCAAATCA TCAACACTGC     1740

CTCAATTCAG TCTCTCATCT GCAATAACGT GAAGGGCTGT CCCTTTACTT CATTCAGTGT     1800

TCCAGATCCA GAGCTCATTA AAACAGTCAC CATCAATGCA AGTTCTTCCC GCTCCGGACT     1860

AGATGATATC AATCCCACAG TACTACTAAA AGAACGTTCG ACTGAACTGT AGAAGTCTAA     1920

TGATCATATT TATTTATTTA TATGAACCAT GTCTATTAAT TTAATTATTT AATAATATTT     1980

ATATTAAACT CCTTATGTTA CTTAACATCT TCTGTAACAG AAGTCAGTAC TCCTGTTGCG     2040

GAGAAAGGAG TCATACTTGT GAAGACTTTT ATGTCACTAC TCTAAAGATT TTGCTGTTGC     2100

TGTTAAGTTT GGAAAACAGT TTTTATTCTG TTTTATAAAC CAGAGAGAAA TGAGTTTGA     2160

CGTCTTTTTA CTTGAATTTC AACTTATATT ATAAGAACGA AGTAAAGAT GTTTGAATAC     2220

TTAAACACTA TCACAAGATG GCAAAATGCT GAAAGTTTTT ACACTGTCGA TGTTTCCAAT     2280

GCATCTTCCA TGATGCATTA GAAGTAACTA ATGTTTGAAA TTTTAAAGTA CTTTTGGGTA     2340

TTTTTCTGTC ATCAAACAAA ACAGGTATCA GTGCATTATT AAATGAATAT TTAAATTAGA     2400

CATTACCAGT AATTTCATGT CTACTTTTTA AAATCAGCAA TGAAACAATA ATTTGAAATT     2460

TCTAAATTCA TAGGGTAGAA TCACCTGTAA AGCTTGTTT GATTTCTTAA AGTTATTAAA     2520

CTTGTACATA TACCAAAAAG AAGCTGTCTT GGATTTAAAT CTGTAAAATC AGATGAAATT     2580
```

```
TTACTACAAT TGCTTGTTAA AATATTTTAT AAGTGATGTT CCTTTTTCAC CAAGAGTATA    2640

AACCTTTTTA GTGTGACTGT TAAAACTTCC TTTTAAATCA AAATGCCAAA TTTATTAAGG    2700

TGGTGGAGCC ACTGCAGTGT TATCTCAAAA TAAGAATATC CTGTTGAGAT ATTCCAGAAT    2760

CTGTTTATAT GGCTGGTAAC ATGTAAAAAC CCCATAACCC CGCCAAAAGG GGTCCTACCC    2820

TTGAACATAA AGCAATAACC AAAGGAGAAA AGCCCAAATT ATTGGTTCCA AATTTAGGGT    2880

TTAAACTTTT TGAAGCAAAC TTTTTTTTAG CCTTGTGCAC TGCAGACCTG GTACTCAGAT    2940

TTTGCTATGA GGTTAATGAA GTACCAAGCT GTGCTTGAAT AACGATATGT TTTCTCAGAT    3000

TTTCTGTTGT ACAGTTTAAT TTAGCAGTCC ATATCACATT GCAAAGTAG  CAATGACCTC    3060

ATAAAATACC TCTTCAAAAT GCTTAAATTC ATTTCACACA TTAATTTTAT CTCAGTCTTG    3120

AAGCCAATTC AGTAGGTGCA TTGGAATCAA GCCTGGCTAC CTGCATGCTG TTCCTTTTCT    3180

TTTCTTCTTT TAGCCATTTT GCTAAGAGAC ACAGTCTTCT CAAACACTTC GTTTCTCCTA    3240

TTTTGTTTTA CTAGTTTTAA GATCAGAGTT CACTTTCTTT GGACTCTGCC TATATTTTCT    3300

TACCTGAACT TTTGCAAGTT TTCAGGTAAA CCTCAGCTCA GGACTGCTAT TTAGCTCCTC    3360

TTAAGAAGAT TAAAAAAAAA AAAAAAG                                       3387

(2) INFORMATION FOR SEQ ID NO: 20:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Met Leu Ala Arg Ala Leu Leu Leu Cys Ala Val Leu Ala
 1               5                  10

(2) INFORMATION FOR SEQ ID NO: 21:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

CTAGCTAGCT A                                                          11

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

GGGGCAGGAA AGCAGCATTC T                                               21

(2) INFORMATION FOR SEQ ID NO: 23:

(i) SEQUENCE CHARACTERISTICS:
        (A) LENGTH: 12 base pairs
```

-continued

```
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 23:

TCGATCGATC GA                                                          12
```